United States Patent [19]

Manfre

[11] Patent Number: 5,719,317
[45] Date of Patent: Feb. 17, 1998

[54] PROCESS FOR THE PREPARATION OF NITROBENZENE DERIVATIVES

[75] Inventor: Franco Manfre, Limeil-Brevannes, France

[73] Assignee: Rhone-Poulenc Rorer S.A., Antony, France

[21] Appl. No.: 809,778

[22] PCT Filed: Sep. 27, 1995

[86] PCT No.: PCT/FR95/01241

§ 371 Date: Mar. 28, 1997

§ 102(e) Date: Mar. 28, 1997

[87] PCT Pub. No.: WO96/10010

PCT Pub. Date: Apr. 4, 1996

[30] Foreign Application Priority Data

Sep. 29, 1994 [FR] France ................. 94 11657

[51] Int. Cl.⁶ .................................................. C07C 205/00
[52] U.S. Cl. .................................. 562/434; 562/438
[58] Field of Search .................................... 562/438

[56] References Cited

U.S. PATENT DOCUMENTS

| | | |
|---|---|---|
| 4,659,862 | 4/1987 | Rajanbabu . |
| 4,859,232 | 8/1989 | Singh . |

FOREIGN PATENT DOCUMENTS

| | | | |
|---|---|---|---|
| 1 228 596 | 4/1971 | United Kingdom . | |

OTHER PUBLICATIONS

Cortese et al., "Palladium–Catalyzed Reductions of Halo–and Nitroaromatic Compounds with Triethylammonium Formate", *Journal of Organic Chemistry*, 42(22):3491–3494 (1977).

*Primary Examiner*—Paul J. Killos
*Attorney, Agent, or Firm*—Finnegan, Henderson, Farabow, Garrett & Dunner, L.L.P.

[57] ABSTRACT

A method for preparing a compound of formula (I), wherein $R_1$ and $R_2$, which are the same or different, are a hydrogen atom or an alkyl or alkoxy radical, or $R_1$ and $R_2$, taken together with the carbon atom to which they are attached, form a cycloalkyl radical containing 3–6 carbon atoms. The method comprises dehalogenating a derivative of formula (II), wherein $R_1$ and $R_2$ have the same meanings as in formula (1) and Hal is a chlorine or bromine atom, using 1–2 mol of triethylammonium formate, in the presence of 0.002–0.1 mol of coal-borne palladium per mol of the compound of formula (II), in acetonitrile or tetrahydrofuran and at a temperature between 50° C. and the boiling point of the reaction medium.

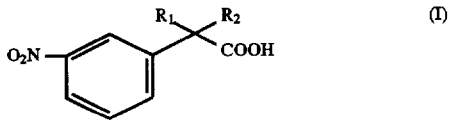

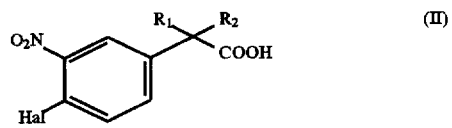

10 Claims, No Drawings

PROCESS FOR THE PREPARATION OF NITROBENZENE DERIVATIVES

The present invention relates to a process for the preparation of nitrobenzene derivatives of formula:

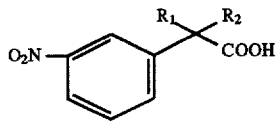

in which $R_1$ and $R_2$, which may be identical or different, represent a hydrogen atom or an alkyl radical containing 1 to 6 carbon atoms in a straight or branched chain or an alkoxy radical containing 1 to 6 carbon atoms in a straight or branched chain, or alternatively $R_1$ and $R_2$, together with the carbon atom to which they are attached, form a cycloalkyl radical containing 3 to 6 carbon atoms, these derivatives being useful in particular as intermediates for the preparation of pharmaceutical products (Patent WO 91/12, 264) or as antidotes for certain insecticides (U.S. Pat. No. 4,859,232).

It is known to prepare these compounds by acid hydrolysis of the corresponding nitriles, which are themselves obtained from the corresponding halo derivatives and an alkali metal cyanide (E. Felder, J. Med. Chem., 13, 559 (1970) and U.S. Pat. No. 4,859,232). The use of alkali metal cyanide may pose pollution problems at the industrial level.

Moreover, it is known to dehalogenate halonitrobenzenes using triethylammonium formate, in the presence of palladium-on-charcoal, in a closed medium, without solvent and at a temperature of 100° C. (N. A. Cortese et al., J. Org. Chem., 42, 22, 3491–3494 (1977)). Since this process is performed in a closed median and at 100° C., it is difficult to industrialize. Furthermore, when applied to the preparation of compounds of formula (I), this process leads to a mixture of 3 products (expected product of formula (I), starting material and a dehalogenated product but in which the nitro is reduced to amino) which are difficult to separate, and the yield of expected product is low.

A non-polluting industrial process has now been found, which allows the pure compounds of formula (I) to be obtained in good yields.

This process consists in dehalogenating a derivative of formula:

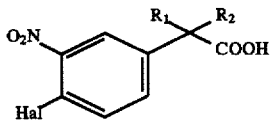

in which $R_1$ and $R_2$ have the same meanings as in formula (I) and Hal represents a chlorine or bromine atom, under atmospheric pressure, using 1 to 2 mol of triethylammonium formate, in the presence of 0.002 to 0.1 mol of palladium-on-charcoal per mole of compound of formula (II), in acetonitrile or tetrahydrofuran, at a temperature between 50° C. and the boiling point of the reaction medium.

This reaction is preferably carried out under inert atmosphere (for example nitrogen).

It is particularly advantageous to use 1.5 mol of triethylammonium formate per 1 mol of derivative of formula (II).

The triethylammonium formate may be formed in situ from 2 molar equivalents of triethylamine and 1.5 molar equivalents of formic acid.

5% palladium-on-charcoal is preferably used and, in particular, 0.01 mol of 5% palladium-on-charcoal per mole of compound (II).

The preferred amount of acetonitrile or tetrahydrofuran is between 5 and 15 weight equivalents relative to the compound of formula (II), and in particular 10 equivalents.

The reaction temperature is preferably in the region of 80° C.

The derivatives of formula (II) may be obtained by application or adaptation of the process described in Patent DE 22100418 or by nitration of the corresponding halo derivatives as described in the examples.

The examples which follow illustrate the invention.

EXAMPLE 1

16.5 ml of formic acid are added over 5 minutes to a round-bottomed flask, under inert atmosphere, containing 67.7 g of (RS)-2-(4-chloro-3-nitrophenyl) propionic acid, 87 ml of triethylamine and 6.1 g of 5% palladium-on-charcoal in 680 ml of acetonitrile. The reaction medium is heated at reflux for 18 hours and, after cooling to a temperature in the region of 20° C., is then filtered through Celite. The filtrate is evaporated to dryness under reduced pressure and taken up in 500 ml of water and 400 ml of ethyl acetate. The organic phase is separated out after settling has taken place and the aqueous phase is extracted with twice 200 ml of ethyl acetate. The combined organic phases are dried over magnesium sulphate and concentrated to dryness under reduced pressure at 40° C. 53 g of 2-(3-nitrophenyl) propionic acid are thus obtained in the form of a brown oil [IR spectrum ($CH_2Cl_2$, cm$^{-1}$) $\delta$OH acid: 3250–2450; $\gamma$CH Aliph.: 2985–2940; $\gamma$C=0: 1715; $\gamma^a NO_2$: 1535; $\gamma^s NO_2$: 1355; $\gamma$Ph m-subst.: 690; NMR spectrum (DMSO-$d_6$, 200 MHz): 1.45 (d, J=7 Hz, 3H); 3.9 (q, J=7 Hz, 1H); 7.6 (t, J=7 Hz, 1H); 7.8 (d, J=7 Hz, 1H); 8.1 (d, J=7 Hz, 1H); 8.15 (s, 1H); 12.5 (broad s, acidic OH)].

2-(4-Chloro-3-nitrophenyl) propionic acid may be prepared according to Patent DE 2,210,418.

EXAMPLE 2

The procedure is similar to that described in Example 1, but starting with 6.3 g of 2-(4-chloro-3-nitrophenyl)-2-methylpropionic acid, 7.62 ml of triethylamine, 0.6 g of 5% palladium-on-charcoal and 1.46 ml of formic acid in 100 ml of acetonitrile. 5.0 g of 2-(3-nitrophenyl)-2-methylpropionic acid are thus obtained in the form of an orange oil [NMR spectrum (DMSO-$d_6$, 200 MHz): 1.57 (s, 6H); 7.65 (t, J=7 Hz, 1H); 7.9 (d, J=7 Hz, 1H); 8.13 (d, J=7 Hz, 1H); 8.15 (s, 1H); 12.5 (broad s, acidic OH)].

2-(4-Chloro-3-nitrophenyl)-2-methylpropionic acid may be prepared in the following way: to a suspension of 5.35 g of 2-(4-chlorophenyl)-2-methylpropionic acid in 50 ml of concentrated sulphuric acid, cooled to a temperature in the region of 5° C., is added dropwise a solution containing 2.65 g of potassium nitrate in 10 ml of concentrated sulphuric acid, while maintaining the reaction medium at this same temperature. The stirring is continued for one hour and the reaction mixture is then poured, with stirring, onto 250 g of crushed ice. The white solid obtained is separated out by filtration, washed with twice 100 ml of water and air-dried. 6.4 g of 2-(4-chloro-3-nitrophenyl)-2-methylpropionic acid, melting at 157° C., are thus obtained.

Comparative Example according to the process by N.A. Cortese.

A round-bottomed flask, maintained under inert atmosphere, containing 1 g of (RS)-2-(4-chloro-3-nitrophenyl) propionic acid, 0.9 ml of triethylamine, 90 mg of 5% palladium-on-charcoal and 0.2 ml of formic acid is heated for 4 hours with stirring at a temperature in the region of 100° C. After cooling to a temperature in the region of 20° C., the thick reaction medium is taken up in 20 ml of $CH_2Cl_2$ and then filtered through Celite. The filtrate is washed successively with 10 ml of aqueous 1N hydrochloric acid solution and 10 ml of water, dried over magnesium sulphate and concentrated to dryness under reduced pressure at 40° C. 0.97 g of a brown oil is thus obtained as a mixture of (RS)-2-(4-chloro-3-nitrophenyl)propionic acid, (RS)-2-(3-nitrophenyl)propionic acid and (RS)-2-(3-aminophenyl) propionic acid in respective molar ratios of 25, 70 and 3 (expressed as percentages).

I claim:

1. A process for preparing nitrobenzene derivatives of formula (I):

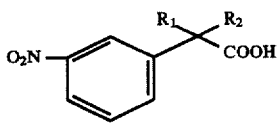
(I)

in which $R_1$ and $R_2$, which may be identical or different, represent a hydrogen atom or an alkyl radical containing from 1 to 6 carbon atoms in a straight or branched chain or an alkoxy radical containing from 1 to 6 carbon atoms in a straight or branched chain, or alternatively $R_1$ and $R_2$, together with the carbon atom to which they are attached, form a cycloalkyl radical containing from 3 to 6 carbon atoms, said process comprising dehalogenating a derivative of formula (II):

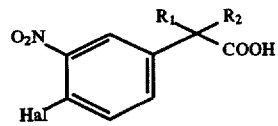
(II)

in which $R_1$ and $R_2$ have the same meanings as in formula (I) and Hal represents a chlorine or bromine atom, under atmospheric pressure with 1 to 2 mol of triethylammonium formate, in the presence of 0.002 to 0.1 mol of palladium-on-charcoal per mole of compound of formula (II), in a reaction medium of acetonitrile or tetrahydrofuran, and at a temperature ranging from 50° C. to the boiling point of the reaction medium.

2. A process according to claim 1, wherein said dehalogenating occurs under inert atmosphere.

3. A process according to claim 1, wherein 1.5 mol of triethylammonium formate are present per 1 mol of derivative of formula (II).

4. A process according to claim 1, wherein said triethylammonium formate is formed in situ.

5. A process according to claim 1, wherein said ammonium formate is prepared from 2 molar equivalents of triethylamine and 1.5 molar equivalents of formic acid.

6. A process according to claim 1, wherein 5% palladium-on-charcoal is present.

7. A process according to claim 1, wherein 0.01 mol of 5% palladium-on-charcoal is present per mole of compound (II).

8. A process according to claim 1, wherein from 5 to 15 weight equivalents of acetonitrile or tetrahydrofuran are present relative to the compound of formula (II).

9. A process according to claim 8, wherein 10 equivalents of acetonitrile or tetrahydrofuran are present.

10. A process according to claim 1, wherein said dehalogenating occurs at a temperature of about 80° C.

* * * * *